United States Patent
O'Lenick et al.

(10) Patent No.: US 9,283,168 B2
(45) Date of Patent: Mar. 15, 2016

(54) COMPLEX POLYOL POLYESTERS

(71) Applicants: Kevin Anthony O'Lenick, Dacula, GA (US); Thomas George O'Lenick, Dacula, GA (US)

(72) Inventors: Kevin Anthony O'Lenick, Dacula, GA (US); Thomas George O'Lenick, Dacula, GA (US)

(73) Assignee: SurfaTECH Corporation, Lawrenceville, GA (US)

( * ) Notice: Subject to any disclaimer, the term of this patent is extended or adjusted under 35 U.S.C. 154(b) by 156 days.

(21) Appl. No.: 13/999,068

(22) Filed: Jan. 10, 2014

(65) Prior Publication Data

US 2015/0196479 A1 Jul. 16, 2015

Related U.S. Application Data

(63) Continuation-in-part of application No. 13/986,523, filed on May 13, 2013, now abandoned, which is a continuation-in-part of application No. 12/930,515, filed on Jan. 10, 2011, now Pat. No. 8,455,670.

(60) Provisional application No. 61/459,348, filed on Dec. 13, 2010.

(51) Int. Cl.
| | | |
|---|---|---|
| *A61K 31/765* | (2006.01) | |
| *A61K 8/85* | (2006.01) | |
| *A61Q 19/00* | (2006.01) | |
| *C08G 63/553* | (2006.01) | |
| *C08G 63/676* | (2006.01) | |
| *C08G 63/199* | (2006.01) | |
| *C08G 63/12* | (2006.01) | |
| *C08G 63/16* | (2006.01) | |
| *C08G 63/137* | (2006.01) | |
| *A61K 8/72* | (2006.01) | |

(52) U.S. Cl.
CPC . *A61K 8/85* (2013.01); *A61Q 19/00* (2013.01); *C08G 63/553* (2013.01); *C08G 63/676* (2013.01); *A61K 8/72* (2013.01); *C08G 63/12* (2013.01); *C08G 63/137* (2013.01); *C08G 63/16* (2013.01); *C08G 63/199* (2013.01)

(58) Field of Classification Search
None
See application file for complete search history.

*Primary Examiner* — James Rogers

(57) ABSTRACT

The present invention is directed to a series of polyesters that are made by the reaction of a diacid with a pre-formed mono-hydroxy, di-hydroxy and optionally a tri-hydroxy ester of polyols selected from pentaerythritol, di pentaerythritol tri-methylolpropane and mixtures thereof. When reacted in the sequence shown, that is pre-formation of the mono-ester, di-ester and tri-ester, selection of the proper ratio of one to the other and then and only then reacted with the diacid, do these polyesters remain free of a gel and form cosmetically elegant oil phases.

3 Claims, No Drawings

COMPLEX POLYOL POLYESTERS

RELATED APPLICATIONS

This application is a continuation in part of Ser. No. 13/986,523, which is in turn a continuation in part of co-pending application Ser. No. 12/930,515, which in turn claims priority to and benefit of U.S. Provisional Application Nos. 61/459,348, filed Dec. 13, 2010, the disclosures of each of which are incorporated herein for all purposes.

FIELD OF THE INVENTION

The present invention is directed to a series of polyesters made by the reaction of a mono-hydroxy ester, a di-hydroxy ester and a tri-hydroxy ester with diacids. The mono-hydroxy acid is a chain terminator, the di-hydroxy acid is a chain extender and the tri-hydroxy acid is a crosslinker. We have determined that one must make the individual components before reaction with the diacids, to avoid a gel and a useless product.

BACKGROUND OF THE INVENTION

Cosmetic formulations applied to the skin and must have four key functions, (1) providing the cosmetic benefit sought (emmoliency, humectancy, smoothing, sun protection and the like; (2) provide cosmetic elegance when so applied; (3) be free of undesired reactive species like free vinyl monomer; and (4) be cost effective. The cosmetic chemist has long sought after this combination of properties.

Historically, the selection of materials that provide the oil phase for emulsions, serums and lotions have been made from mineral oil, petrolatum, naturally occurring oils and fatty esters. These materials while well used lack the ability to modify the feel, flow and film forming properties on the skin.

In making polyesters, one can either add all reactants, or pre-esterify the individual reactants followed by the reaction with diacids. We have learned that the pre-esterification of the intermediates followed by the reaction with diacids results in highly desirable polyesters, while reacting all raw materials together results in a gel.

OBJECTIVE OF THE INVENTION

The present invention is aimed at providing a series of polyesters that are made in a sequential way by first making mono hydroxyl esters of polyol compounds selected from the group consisting of pentaerythritol, dipentaerythritol and trimethylol propane which have been made using fatty acids, next in a separate reactor making di hydroxyl esters of polyol compounds selected from the group consisting of pentaerythritol, dipentaerythritol and trimethylol propane, followed by crosslinking the mono and di hydroxyl, one having the high melting point and the other the low melting point acids esterified thereon, with a diacids to make a polyester. This is because the di hydroxyl functional compound can polymerize with the diacids to form a chain and the mono-functional compound can only terminate the reaction.

Other objectives of the invention will become clear as one reads the specification. All patents cited herein are incorporated herein by reference. All percentages are percentages by weight, all temperatures are degrees centigrade, unless specifically stated otherwise.

SUMMARY OF THE INVENTION

The present invention is directed to a series of polyesters made by reacting a mono-hydroxy polyol ester, a di-hydroxy poloyl ester and optionally a tri-hydroxy polyester with a diacid to make polyesters.

The polymers of the present invention are not made using free radical chemistry, which can have residual and very undesirable vinyl monomers left after the reaction. These polymers are made by esterification chemistry, using fatty acids, diacids and polyols. The resulting polymers contain well-known reactants that are well known, and have a molecular weight above 1500 Daltons, which minimizes their ability to penetrate the skin.

This combination of properties result in what we refer to as epigenomic friendly compounds, staying on the skin and providing benefits to the skin without penetration and causing irritation and inflammation.

DETAILED DESCRIPTION OF THE INVENTION

The polyesters of the present invention have the following structure;

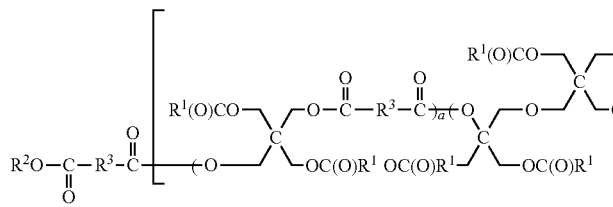

wherein;

$R^2$ is selected from the group consisting of

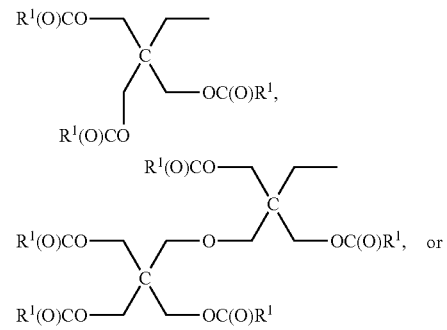

-continued

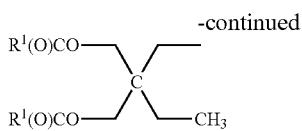

with the proviso that $R^2$ is not mixtures there of;
$R^1$ is selected from the group consisting of;
(1) alkyl and alkylene derived from a fatty acid having a melting point below 30° C.,
(2) alkyl or alkylene derived from a fatty acid having a melting point above 40° C. with the proviso that R' is not mixtures thereof;
$R^3$ is selected from the group consisting of;
(1) —$(CH_2)_n$—
n is an integer from 2 to 10;
(2) a cyclic unsaturated having the structure

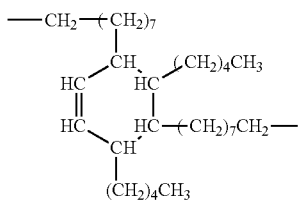

and
(3) a saturated cyclic having the following structure;

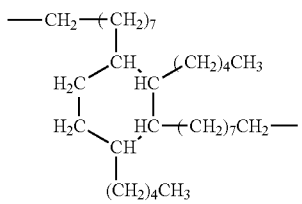

n is an integer ranging from 5 to 20;
a is an integer ranging from to 0 to 20
b is an integer ranging from 0 to 20,
c is an integer ranging from 0 to 20
d is an integer ranging from 0 to 20 with the proviso that a+b+c+d=n.

Another aspect of the present invention is a series if esters that are used as intermediates in the preparation of the compounds of the present invention selected from the group consisting of;

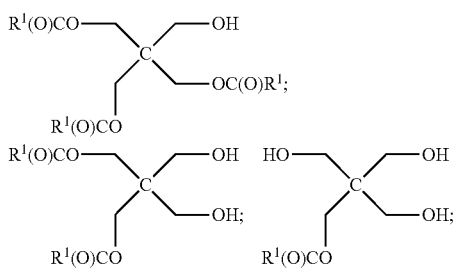

wherein;
$R^1$ is selected from the group consisting of
(1) alkyl and alkylene derived from a fatty acid having a melting point below 30° C. and
(2) alkyl or alkylene derived from a fatty acid having a melting point above 40° C. with the proviso that $R^4$ is not mixtures thereof.

Still another aspect of the present invention is esters that are used as intermediates in the preparation of the compounds of the present invention selected from;

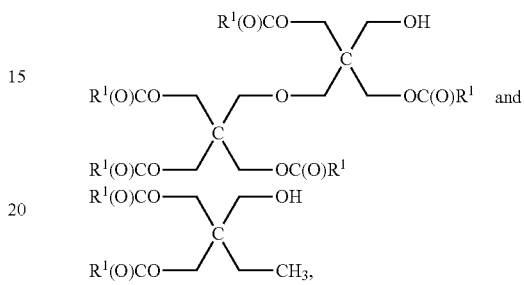

wherein;
$R^1$ is selected from:
(1) alkyl and alkylene derived from a fatty acid having a melting point below 30° C. and
(2) alkyl or alkylene derived from a fatty acid having a melting point above 40° C. with the proviso that $R^5$ is not mixtures thereof.

Another aspect of the present invention is a polyester made by the reaction of:
(a) a mono-hydroxy substituted complex ester selected from the group consisting of:
(i) a pentaerythritol tri-ester having the structure:

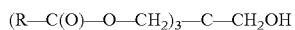

(ii) a dipentaerythritol penta-ester having the structure:

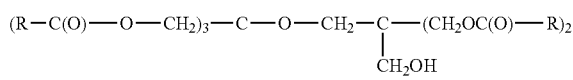

(iii) a trimethylol propane di-ester having the structure:

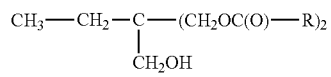

wherein R is alkyl having 17 to 21 carbon atoms and mixtures thereof;
(iv) and mixtures thereof;
(b) a di-hydroxy substituted complex ester selected from the group consisting of:
(i) a pentaerythritol di-ester having the structure:

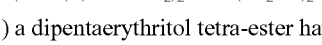

(ii) a dipentaerythritol tetra-ester having the structure:

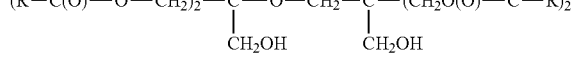

(iii) a trimethylol propane di-ester having the structure:

$$CH_3-CH_2-\underset{\underset{CH_2OH}{|}}{C}-(CH_2OC(O)-R)_2$$

wherein R is alkyl having 17 to 21 carbon atoms and mixtures thereof;
(iv) and mixtures thereof;
and optionally;
(c) a tri-hydroxy substituted complex ester selected from the group consisting of:
(i) a pentaerythritol mono-ester having the structure:

$$(R-C(O)-O-CH_2)_3-C-CH_2OH$$

(ii) a dipentaerythritol tri-ester having the structure:

$$(R-C(O)-O-CH_2)_2-\underset{\underset{CH_2OH}{|}}{C}-O-CH_2-\underset{\underset{(CH_2OH)}{|}}{C}-CH_2O(O)-C-R$$

wherein R is alkyl having 17 to 21 carbon atoms and mixtures thereof;
and
(d) a diacid selected from the group consisting of
(i) dimer acid having the following structure:

[structure of dimer acid]

(ii) hydrogenated dimer acid having to the following structure:

[structure of hydrogenated dimer acid]

(iii) a dicarboxylic acid having following structure;

$$HO-\underset{\underset{}{||}}{\overset{O}{C}}-(CH_2)_c-\underset{\underset{}{||}}{\overset{O}{C}}-OH$$

wherein;
c is an integer ranging from 1 to 10.
R is alkyl having 7 to 21 carbon atoms and mixtures thereof.

Another aspect of the present invention is a process for conditioning skin, which comprises contacting the skin with an effective conditioning concentration of a polyester made by the reaction of:
(a) a mono-hydroxy substituted complex ester selected from the group consisting of:
(i) a pentaerythritol tri-ester having the structure:

$$(R-C(O)-O-CH_2)_3-C-CH_2OH$$

(ii) a dipentaerythritol penta-ester having the structure:

$$(R-C(O)-O-CH_2)_3-C-O-CH_2-\underset{\underset{CH_2OH}{|}}{C}-(CH_2OC(O)-R)_2$$

(iii) a trimethylol propane di-ester having the structure:

$$CH_3-CH_2-\underset{\underset{CH_2OH}{|}}{C}-(CH_2OC(O)-R)_2$$

wherein R is alkyl having 17 to 21 carbon atoms and mixtures thereof;
(iv) and mixtures thereof;
(b) a di-hydroxy substituted complex ester selected from the group consisting of:
(i) a pentaerythritol di-ester having the structure:

$$(R-C(O)-O-CH_2)_2-C-(CH_2OH)_2$$

(ii) a dipentaerythritol tetra-ester having the structure:

$$(R-C(O)-O-CH_2)_2-\underset{\underset{CH_2OH}{|}}{C}-O-CH_2-\underset{\underset{CH_2OH}{|}}{C}-(CH_2O(O)-C-R)_2$$

(iii) a trimethylol propane di-ester having the structure:

$$CH_3-CH_2-\underset{\underset{CH_2OH}{|}}{C}-(CH_2OC(O)-R)_2$$

wherein R is alkyl having 17 to 21 carbon atoms and mixtures thereof;
(iv) and mixtures thereof;
and optionally
(c) a tri-hydroxy substituted complex ester selected from the group consisting of:
(i) a pentaerythritol monoester having the structure:

$$R-C(O)-O-CH_2-C-(CH_2OH)_3$$

(ii) a dipentaerythritol tri-ester having the structure:

$$(R-C(O)-O-CH_2)_2-\underset{\underset{CH_2OH}{|}}{C}-O-CH_2-\underset{\underset{(CH_2OH)_2}{|}}{C}-CH_2O(O)-C-R$$

wherein R is alkyl having 17 to 21 carbon atoms and mixtures thereof;
and
(d) a diacid selected from the group consisting of
(i) dimer acid having the following structure:

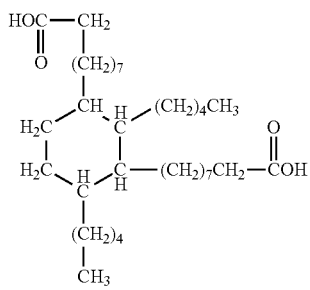

(ii) hydrogenated dimer acid having to the following structure:

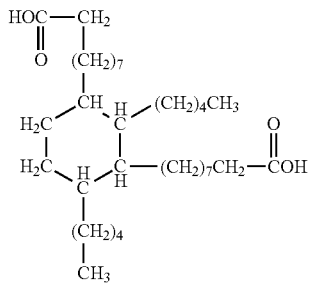

(iii) a dicarboxylic acid having following structure;

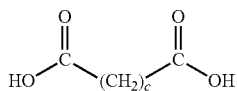

wherein;
c is an integer ranging from 1 to 10;
and
(iv) mixtures thereof.

In the present invention, the mono hydroxyl containing and the di hydroxyl containing ester intermediate are reacted with the proper amount of diacids and linked together to form the polymer of the present invention.

Preferred Embodiment

In a preferred embodiment said mono hydroxy substituted complex ester is a pentaerythritol tri-ester, said dihydroxy substituted complex ester is a dipentaerythritol tetra-ester.

In a preferred embodiment said mono hydroxy substituted complex ester is a dipentaerythritol penta-ester, said dihydroxy substituted complex ester is a pentaerythritol di-ester and said trihydroxy substituted complex ester is a a pentaerythritol monoester.

In a preferred embodiment said mono hydroxy substituted complex ester is a dipentaerythritol penta-ester, said di-hydroxy substituted complex ester is a pentaerythritol di-ester.

In a preferred embodiment said effective conditioning concentration ranges from 0.1% to 15.0% by weight.

Raw Materials

Pentaerythritol

Pentaerythritol is a useful raw material in the synthesis of the compounds of the present invention. They are commercially available from a variety of sources including Sigma Aldrich online at http://www.sigmaaldrich.com. It has the following structure;

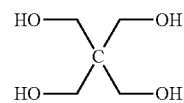

Dipentaerythritol

Dipentaerythritol is a useful raw material in the synthesis of the compounds of the present invention. They are commercially available from a variety of sources including Sigma Aldrich online at http://www.sigmaaldrich.com. It has the following structure:

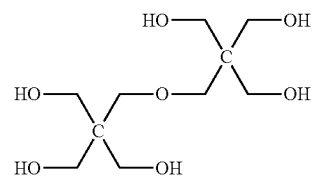 [SMILES: OCC(CO)(CO)COCC(CO)(CO)CO]

Trimethylol Propane

Trimethylol propane is a useful raw material in the synthesis of the compounds of the present invention. They are commercially available from a variety of sources including Sigma Aldrich online. It has the following structure:

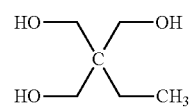

Example 1

Dimer Acid

Dimer acid is an item of commerce available commercially from Cognis Corporation. It has the following structure:

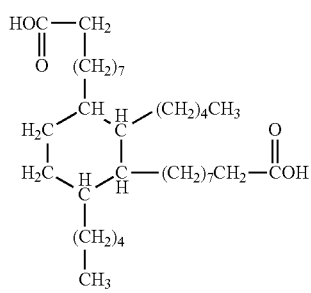

Example 2

Hydrogenated Dimer Acid

Hydrogenated dimer acid is an item of commerce available commercially from Henkel Corporation. It conforms to the following structure:

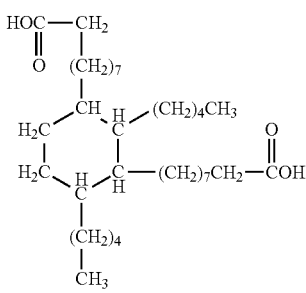

Dicarboxylic Acid

Dicarboxylic acid useful as raw materials in the synthesis of the compounds of the present invention are commercially available from a variety of sources including Cognis. They have following structure;

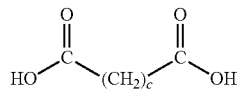

wherein;
c is an integer ranging from 1 to 10.

Saturated Dicarboxylic Acids

| Example | Common Name | c | Molecular Weight |
|---|---|---|---|
| 3 | Malonic | 1 | 104 |
| 4 | Succinic | 2 | 118 |
| 5 | Glutaric | 3 | 132 |
| 6 | Adipic | 4 | 146 |
| 7 | Pimelic | 5 | 160 |
| 8 | Subric | 6 | 174 |
| 9 | Azelaic | 7 | 188 |
| 10 | Sebacic | 8 | 202 |
| 11 | Undecanedioic | 9 | 216 |
| 12 | Dodecanedioic | 10 | 230 |

Fatty Acids

Fatty acids useful in the practice of the present invention are items of commerce commercially available from Cognis.

Fatty Acid Names

Fatty acids useful as raw materials in the preparation of compounds of the present invention are commercially available from a variety of sources including Procter and Gamble of Cincinnati Ohio. The structures are well known to those skilled in the art.

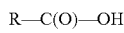

Saturated

| Example | R Formula | Common Name | Molecular Weight |
|---|---|---|---|
| 13 | $C_7H_5$ | Caprylic | 144 |
| 14 | $C_9H_{19}$ | Capric | 172 |
| 15 | $C_{11}H_{23}$ | Lauric | 200 |
| 16 | $C_{13}H_{27}$ | Myristic | 228 |
| 17 | $C_{14}H_{29}$ | Pentadecanoic | 242 |
| 18 | $C_{15}H_{31}$ | Palmitic | 256 |
| 19 | $C_{17}H_{35}$ | Stearic | 284 |
| 20 | $C_{17}H_{35}$ | Isosteric | 284 |
| 21 | $C_{19}H_{39}$ | Arachidinic | 312 |
| 22 | $C_{21}H_{43}$ | Behenic | 340 |
| 23 | $C_{26}H_{53}$ | cetrotic | 396 |
| 24 | $C_{33}H_{67}$ | geddic acid | 508 |

Unsaturated

| Example | R Formula | Common Name | Molecular Weight |
|---|---|---|---|
| 25 | $C_{17}H_{33}$ | Oleic | 282 |
| 26 | $C_{17}H_{31}$ | Linoleic | 280 |
| 27 | $C_{17}H_{29}$ | Linolenic | 278 |
| 28 | $C_{15}H_{29}$ | Palmitoleic | 254 |
| 29 | $C_{13}H_{25}$ | Myristicoleic | 226 |
| 30 | $C_{21}H_{41}$ | Erucic | 338 |

Chain Terminators

Chain terminators are mono-functional molecules, meaning that they only have one reactive hydroxyl site (the others are esterified). The fact that they have only one reactive site means that they cannot be incorporated into the polymer backbone. The moment a chain terminator reacts in a polymerization, the polymer chain is terminated. Since these mono-functional molecules terminate polymer chains, they are employed in polymer chemistry to control molecular weight and functionalize chain ends.

General Procedure

To the specified number of grams of the specified polyol (pentaerythritol, dipentaerythritol or TMP) is added the specified number of grams of the specified fatty acid (examples 13-30). The reaction mixture is heated to 180° C. and held until the acid value fails to drop any further. Product is analyzed and used in the subsequent polymerization step, by reacting it with diacids.

| Pentaerythritol | | Fatty Acid | |
|---|---|---|---|
| Example | Grams | Example | Grams |
| 31 | 18.5 | 13 | 81.5 |
| 32 | 16.6 | 14 | 83.4 |
| 33 | 15.0 | 26 | 85.0 |
| 34 | 13.8 | 17 | 86.2 |
| 35 | 11.8 | 20 | 88.2 |
| 36 | 8.6 | 22 | 91.4 |

| | Pentaerythritol | | Fatty Acid |
|---|---|---|---|
| Example | Grams | Example | Grams |
| 37 | 59.8 | 11 | 190.3 |
| 38 | 52.3 | 12 | 197.8 |
| 39 | 34.5 | 18 | 215.5 |
| 40 | 34.5 | 23 | 215.5 |
| 41 | 35.0 | 24 | 215.0 |
| 42 | 32.5 | 19 | 217.5 |

| | Dipentaerythritol | | Fatty Acid |
|---|---|---|---|
| Example | Grams | Example | Grams |
| 43 | 65.3 | 11 | 184.7 |
| 44 | 57.0 | 12 | 193.0 |
| 45 | 38.0 | 18 | 212.0 |
| 46 | 38.3 | 23 | 211.7 |
| 47 | 38.8 | 24 | 211.2 |
| 48 | 35.8 | 19 | 214.2 |

| | Dipentaerythritol | | Fatty Acid |
|---|---|---|---|
| Example | Grams | Example | Grams |
| 49 | 50.8 | 13 | 199.2 |
| 50 | 45.5 | 14 | 204.5 |
| 51 | 41.5 | 26 | 208.5 |
| 52 | 38.0 | 17 | 212.0 |
| 53 | 32.5 | 20 | 217.5 |
| 54 | 24.0 | 22 | 226.0 |

| | TMP | | Fatty Acid |
|---|---|---|---|
| Example | Grams | Example | Grams |
| 55 | 62.8 | 13 | 187.3 |
| 56 | 56.8 | 14 | 193.3 |
| 57 | 51.8 | 26 | 198.2 |
| 58 | 47.8 | 17 | 202.2 |
| 59 | 41.3 | 20 | 208.7 |
| 60 | 30.5 | 22 | 219.5 |

| | TMP | | Fatty Acid |
|---|---|---|---|
| Example | Grams | Example | Grams |
| 61 | 79.5 | 11 | 170.5 |
| 62 | 70.0 | 12 | 180.0 |
| 63 | 47.8 | 18 | 202.3 |
| 64 | 48.0 | 23 | 202.0 |
| 65 | 48.5 | 24 | 201.5 |
| 66 | 45.3 | 19 | 204.8 |

Monomers

Monomers are molecules that have two reactive hydroxyl sites (all others are esterified on the molecule). They can be easily polymerized by a diacid. These molecules make up the polymer back-bone and control physical properties of the polymer chain.

General Procedure

To the specified number of grams of the specified polyol (pentaerythritol, dipentaerythritol or TMP) is added the specified number of grams of the specified fatty acid (examples 13-30). The reaction mixture is heated to 180° C. and held until the acid value fails to drop any further. Product is analyzed and used in the subsequent polymerization step, by reacting it with diacids.

| | Pentaerythritol | | Fatty Acid |
|---|---|---|---|
| Example | Grams | Example | Grams |
| 67 | 25.4 | 13 | 74.6 |
| 68 | 23.0 | 14 | 77.0 |
| 69 | 21.0 | 26 | 79.0 |
| 70 | 19.3 | 17 | 80.7 |
| 71 | 16.7 | 20 | 83.3 |
| 72 | 12.4 | 22 | 87.6 |

| | Pentaerythritol | | Fatty Acid |
|---|---|---|---|
| Example | Grams | Example | Grams |
| 73 | 32.1 | 11 | 67.9 |
| 74 | 28.3 | 12 | 71.7 |
| 75 | 19.3 | 18 | 80.7 |
| 76 | 19.4 | 23 | 80.6 |
| 77 | 19.7 | 24 | 80.3 |
| 78 | 18.3 | 19 | 81.7 |

| | Dipentaerythritol | | Fatty Acid |
|---|---|---|---|
| Example | Grams | Example | Grams |
| 79 | 60.2 | 13 | 189.8 |
| 80 | 54.5 | 14 | 195.5 |
| 81 | 49.7 | 26 | 200.3 |
| 82 | 45.6 | 17 | 204.4 |
| 83 | 39.3 | 20 | 210.7 |
| 84 | 29.2 | 22 | 220.8 |

| | Dipentaerythritol | | Fatty Acid |
|---|---|---|---|
| Example | Grams | Example | Grams |
| 85 | 76.5 | 11 | 173.5 |
| 86 | 67.4 | 12 | 182.6 |
| 87 | 45.6 | 18 | 204.4 |
| 88 | 26.9 | 23 | 223.1 |
| 89 | 46.2 | 24 | 203.8 |
| 90 | 43.2 | 19 | 206.8 |

| | TMP | | Fatty Acid |
|---|---|---|---|
| Example | Grams | Example | Grams |
| 91 | 40.1 | 13 | 59.9 |
| 92 | 37.0 | 14 | 63.0 |
| 93 | 34.4 | 26 | 65.6 |
| 94 | 32.1 | 17 | 67.9 |
| 95 | 28.3 | 20 | 71.7 |
| 96 | 21.8 | 22 | 78.2 |

|  | TMP | Fatty Acid | |
|---|---|---|---|
| Example | Grams | Example | Grams |
| 97 | 48.2 | 11 | 51.8 |
| 98 | 43.8 | 12 | 56.2 |
| 99 | 32.1 | 18 | 67.9 |
| 100 | 32.2 | 23 | 67.8 |
| 101 | 32.4 | 24 | 67.6 |
| 102 | 30.6 | 19 | 69.4 |

Cross-Linker

Cross-linkers are molecules that have three or more hydroxyl reactive sites (all other hydroxyl groups are esterified). The molecules can link two or more polymer chains together. Thus the term "cross-link". These cross-links are bridges linking two polymer chains together. The physical and thermo-properties of the polymer are drastically changed by cross-linking process. As the cross-linking is increased, the polymer chains become less mobile. This loss of mobility causes the polymer to become brittle and decreases solubility.

General Procedure

To the specified number of grams of the specified polyol (pentaerythritol, dipentaerythritol or TMP) is added the specified number of grams of the specified fatty acid (examples 13-30). The reaction mixture is heated to 180° C. and held until the acid value fails to drop any further. Product is analyzed and used in the subsequent polymerization step, by reacting it with diacids.

|  | Pentaerythritol | Fatty Acid | |
|---|---|---|---|
| Example | Grams | Example | Grams |
| 103 | 101.2 | 13 | 148.8 |
| 104 | 93.4 | 14 | 156.6 |
| 105 | 86.7 | 26 | 163.3 |
| 106 | 80.9 | 17 | 169.1 |
| 107 | 71.4 | 20 | 178.6 |
| 108 | 55.2 | 22 | 194.8 |

|  | Pentaerythritol | Fatty Acid | |
|---|---|---|---|
| Example | Grams | Example | Grams |
| 109 | 121.4 | 11 | 128.6 |
| 110 | 110.4 | 12 | 139.6 |
| 111 | 80.9 | 18 | 169.1 |
| 112 | 81.3 | 23 | 168.7 |
| 113 | 81.7 | 24 | 168.3 |
| 114 | 77.3 | 19 | 172.7 |

|  | Dipentaerythritol | Fatty Acid | |
|---|---|---|---|
| Example | Grams | Example | Grams |
| 115 | 74.4 | 13 | 175.6 |
| 116 | 67.7 | 14 | 182.3 |
| 117 | 62.1 | 26 | 187.9 |
| 118 | 57.3 | 17 | 192.7 |
| 119 | 49.8 | 20 | 200.2 |
| 120 | 37.5 | 22 | 212.5 |

|  | Dipentaerythritol | Fatty Acid | |
|---|---|---|---|
| Example | Grams | Example | Grams |
| 121 | 92.6 | 11 | 157.4 |
| 122 | 82.5 | 12 | 167.5 |
| 123 | 57.3 | 18 | 192.7 |
| 124 | 34.6 | 23 | 215.4 |
| 125 | 58.0 | 24 | 192.0 |
| 126 | 54.5 | 19 | 195.5 |

Linear Polymers

General Procedure

A specified number of grams of monomer (examples 67-102), diacid (examples 3-12), and chain terminator (example 31-66) are added into a reaction flask. The reaction mixture is heated to 180° C. and held until the acid value and molecular weight reach a desired value. The polymer is analyzed and used with out further purification.

|  | Monomer | | Diacid | | Chain Terminator | |
|---|---|---|---|---|---|---|
| Example | Example | Grams | Example | Grams | Example | Grams |
| 127 | 67 | 126.3 | 4 | 30.5 | 34 | 93.1 |
| 128 | 68 | 174.7 | 6 | 45.2 | 35 | 30.1 |
| 129 | 77 | 151.1 | 9 | 49.3 | 37 | 49.6 |
| 130 | 78 | 177.0 | 12 | 57.5 | 38 | 15.5 |
| 131 | 81 | 127.8 | 1 | 72.0 | 49 | 50.2 |
| 132 | 82 | 153.8 | 2 | 69.9 | 54 | 26.3 |
| 133 | 85 | 127.8 | 4 | 19.9 | 45 | 102.7 |
| 134 | 86 | 186.7 | 6 | 30.4 | 46 | 33.0 |
| 135 | 95 | 126.7 | 9 | 60.3 | 56 | 63.1 |
| 136 | 96 | 166.8 | 12 | 65.6 | 57 | 17.6 |
| 137 | 99 | 73.9 | 1 | 127.3 | 65 | 48.8 |
| 138 | 100 | 92.7 | 2 | 140.8 | 66 | 16.5 |

Cross-Linked Polymer General Procedure

A specified number of grams of monomer (examples 67-102), diacid (examples 3-12), chain terminator (example 31-66), and cross-linker (examples 103-126) are added into a reaction flask. The reaction mixture is heated to 180° C. and held until the acid value and molecular weight reach a desired value. The polymer is analyzed and used with out further purification.

|  | Monomer | | Diacid | | Cross-linker | | Chain Terminator | |
|---|---|---|---|---|---|---|---|---|
| Example | Example | Grams | Example | Grams | Example | Grams | Example | Grams |
| 139 | 67 | 102.8 | 4 | 36.3 | 103 | 94.8 | 34 | 16.1 |
| 140 | 68 | 166.7 | 6 | 47.6 | 104 | 30.2 | 35 | 5.4 |
| 141 | 77 | 122.8 | 9 | 58.4 | 113 | 50.4 | 37 | 18.5 |
| 142 | 78 | 135.1 | 12 | 72.4 | 114 | 15.8 | 38 | 26.6 |
| 143 | 81 | 99.5 | 1 | 81.8 | 117 | 48.8 | 49 | 19.9 |
| 144 | 82 | 145.0 | 2 | 72.7 | 118 | 26.1 | 54 | 6.1 |
| 145 | 85 | 98.7 | 4 | 22.5 | 124 | 99.6 | 45 | 29.2 |
| 146 | 86 | 176.3 | 6 | 30.2 | 125 | 10.8 | 46 | 32.8 |
| 147 | 95 | 99.1 | 9 | 68.8 | 105 | 61.7 | 56 | 20.5 |

-continued

| | Monomer | | Diacid | | Cross-linker | | Chain Terminator | |
|---|---|---|---|---|---|---|---|---|
| Example | Example | Grams | Example | Grams | Example | Grams | Example | Grams |
| 148 | 96 | 127.8 | 12 | 83.0 | 110 | 17.9 | 57 | 21.4 |
| 149 | 99 | 49.0 | 1 | 123.2 | 119 | 40.5 | 65 | 37.4 |
| 150 | 100 | 83.0 | 2 | 139.1 | 126 | 15.6 | 66 | 12.2 |

Co-Polymer General Procedure

A specified number of grams of monomer 1 (examples 67-102), monomer 2 (examples 67-102), diacid (examples 3-12), and chain terminator (example 31-66) are added into a reaction flask. The reaction mixture is heated to 180° C. and held until the acid value and molecular weight reach a desired value. The polymer is analyzed and used with out further purification.

| | Monomer 1 | | Monomer 2 | | Diacid | | Cross-Link | | Chain Terminator | |
|---|---|---|---|---|---|---|---|---|---|---|
| Example | Example | Grams | Example | Grams | Example | Grams | Example | Grams | Example | Grams |
| 151 | 67 | 101.3 | 100 | 35.7 | 4 | 19.7 | 103 | 0.0 | 34 | 93.3 |
| 152 | 68 | 159.1 | 99 | 12.5 | 6 | 48.0 | 104 | 0.0 | 35 | 30.5 |
| 153 | 77 | 75.7 | 96 | 67.1 | 9 | 57.5 | 113 | 0.0 | 37 | 49.7 |
| 154 | 78 | 95.6 | 95 | 60.9 | 12 | 76.8 | 114 | 0.0 | 38 | 16.7 |
| 155 | 81 | 27.2 | 86 | 80.1 | 1 | 89.3 | 117 | 0.0 | 49 | 53.3 |
| 156 | 82 | 132.1 | 85 | 78.9 | 2 | 125.9 | 118 | 0.0 | 54 | 45.2 |
| 157 | 85 | 69.4 | 82 | 38.8 | 4 | 21.1 | 124 | 27.4 | 45 | 93.4 |
| 158 | 86 | 153.6 | 81 | 29.4 | 6 | 24.5 | 125 | 10.5 | 46 | 31.9 |
| 159 | 95 | 44.5 | 78 | 61.8 | 9 | 69.9 | 105 | 18.4 | 56 | 55.4 |
| 160 | 96 | 13.6 | 77 | 138.4 | 12 | 66.5 | 110 | 17.1 | 57 | 14.4 |
| 161 | 99 | 11.5 | 68 | 49.1 | 1 | 116.0 | 119 | 35.2 | 65 | 38.1 |
| 162 | 100 | 8.3 | 67 | 95.7 | 2 | 131.3 | 126 | 0.0 | 66 | 14.7 |

Applications

The ability to regulate the structure of compounds allows for the preparation of products that have unique properties in skin and sun care. The compounds of the present invention are used to provide a water-resistant film that holds actives on the skin.

The ability to regulate the location of the oil soluble groups in the polymer allows for the alteration of the Partition Coefficient, which determines the solubility of the various actives in the polymer. This ability to alter the partition coefficient of the polymer allows for the ability to engineer a polymer for the specific active that one decides to place on the skin. We refer to these polymers are partition coefficient technology polymers.

Additionally, the ability to place different polyol types in the terminal or internal groups positions of the polymer allows unique products for a slower release of actives. The more "internal" the liquid polymer portion the more "shielded" the active dissolved therein.

The understanding that the monomers need to be premade then reacted with the diacid is absolutely critical in avoiding a gel, which renders the product non-usable. Specifically the mono-hydroxy monomer (chain terminator), di-hydroxy monomer (chain extender) and the tri-hydroxy monomer (crosslinker) will make the products of the present invention unique in both the functional and aesthetics provided on the skin.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein above but rather that the claims be construed as encompassing all the features of patentable novelty which reside in the present invention, including all features which would be treated as equivalents thereof by those skilled in the art to which the invention pertains.

The invention claimed is:

1. A polyester having the following structure;

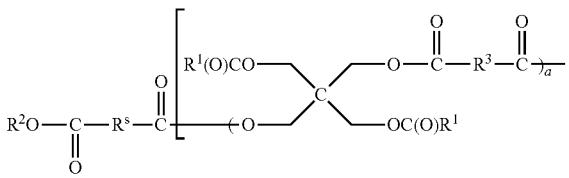

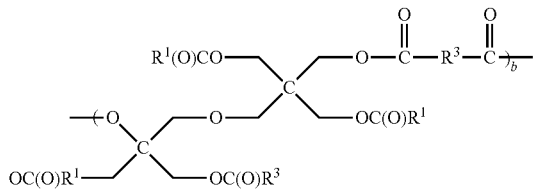

-continued

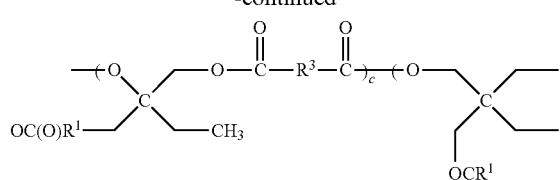

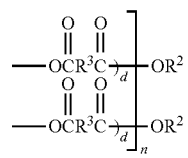

wherein;

$R^1$ is selected from the group consisting of;
  (1) alkyl and alkylene derived from a fatty acid having a melting point below 30° C.,
  (2) alkyl or alkylene derived from a fatty acid having a melting point above 40° C.;

$R^2$ is selected from the group consisting of

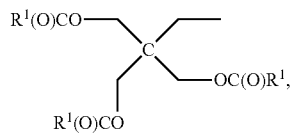

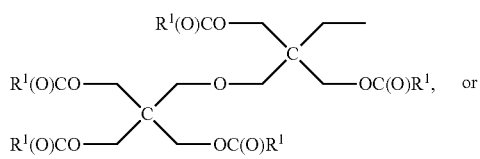

-continued

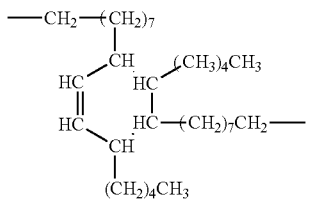

is not mixtures there of;
$R^3$ is selected from the group consisting of;
  (1) —$(CH_2)_x$—
    x is an integer from 2 to 10;
  (2) a cyclic unsaturated having the structure

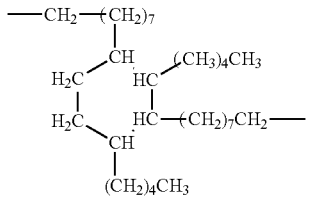

and
(3) a saturated cyclic having the following structure;

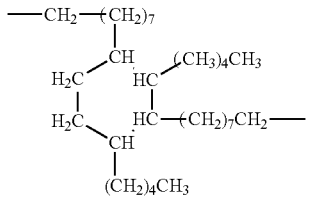

n is an integer ranging from 5 to 20;
a is an integer ranging from to 0 to 20,
b is an integer ranging from 0 to 20,
c is an integer ranging from 0 to 20
d is an integer ranging from 0 to 20 with the proviso that a+b+c+d=n.

2. A process for conditioning skin, which comprises contacting the skin with an effective conditioning concentration of a polyester of claim 1.

3. A process of claim 2 wherein said effective conditioning concentration ranges from 0.1 to 15% by weight.

* * * * *